(12) United States Patent
Park et al.

(10) Patent No.: US 8,043,203 B2
(45) Date of Patent: Oct. 25, 2011

(54) METHOD AND DEVICE FOR TINNITUS THERAPY

(75) Inventors: Jeong-je Park, Yongin-si (KR);
Kyung-ho Kim, Yongin-si (KR);
Kun-kook Park, Suwon-si (KR);
Youn-ho Kim, Hwaseong-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 1290 days.

(21) Appl. No.: 11/339,522

(22) Filed: Jan. 26, 2006

(65) Prior Publication Data

US 2006/0167335 A1 Jul. 27, 2006

(30) Foreign Application Priority Data

Jan. 26, 2005 (KR) .................... 10-2005-0007238

(51) Int. Cl.
*H04R 25/00* (2006.01)
(52) U.S. Cl. .................. 600/25; 381/73.1; 381/312

(58) Field of Classification Search ............ 600/25, 600/26, 28; 381/73.1, 71.8–71.14, 312–331; 128/897–898
See application file for complete search history.

(56) References Cited

U.S. PATENT DOCUMENTS

| 4,038,496 A * | 7/1977 | Feezor ............................ 73/585 |
| 2004/0131200 A1* | 7/2004 | Davis ........................... 381/73.1 |

* cited by examiner

*Primary Examiner* — Charles A Marmor, II
*Assistant Examiner* — Carrie R Dorna
(74) *Attorney, Agent, or Firm* — Sughrue Mion, PLLC

(57) ABSTRACT

A method and device for tinnitus therapy. The method includes generating pure sounds, each having a predetermined frequency, within an audible range, and waiting for a user to press an input button when the user hears the pure sound. Then, the hearing characteristics of the user are interpreted in conjunction with equal loudness contours. From this interpretation, either a tinnitus masking method or a tinnitus retraining therapy are selected according to the hearing characteristics of the user.

8 Claims, 5 Drawing Sheets

METHOD AND DEVICE FOR TINNITUS THERAPY

CROSS-REFERENCE TO RELATED PATENT APPLICATIONS

This application claims priority from Korean Patent Application No. 10-2005-0007238, filed on Jan. 26, 2005, in the Korean Intellectual Property Office, the disclosure of which is incorporated herein in its entirety by reference.

BACKGROUND OF THE INVENTION

1. Field of the Invention

Apparatuses and methods consistent with the present invention relate to tinnitus therapy, and more particularly, to treating tinnitus by selecting either a masking method or a retraining therapy.

2. Description of the Related Art

Tinnitus is a condition which causes a person to perceive noises in their ear when no external sound is present, due to an abnormal stimulus of a hearing nerve. It is caused by a disease of the ear, mental excitement, or a vascular disorder. Tinnitus often takes the form of a ringing sound, which may be intermittent or constant, varies from low to high pitch, and occurs usually in one ear or sometimes in both ears.

Between 15 and 20 percent of adults have experienced some type of tinnitus, and 4 percent of those have suffered from serious symptoms. The most typical cause of the tinnitus is damage to the hearing nerve, and in middle age, the hearing nerve can be somewhat degenerated or damaged, and thereby, ringing in the ears may occur. Recently it has been noted that exposure to loud noises such as industrial noise, loud music, and the use of stereo headphones commonly induces tinnitus. Other causes vary from too much earwax to a serious disease.

As the causes of tinnitus are diverse, treatments are varied, including medication, surgery for conditions such as a brain tumor, vascular disease and muscle disease, a masking method which masks the perception of the tinnitus using a hearing aid-style device that produces a noise similar to, but louder than the tinnitus sound, and a tinnitus retraining therapy in which a quieter sound than the tinnitus is constantly provided, ranging over a wide frequency spectrum, to treat the tinnitus without accompanying hearing loss.

Tinnitus treatments have been continuously studied to develop various tinnitus treatment devices. U.S. Pat. No. 6,047,074 entitled 'Programmable hearing aid operable in a mode for tinnitus therapy' discloses a programmable digital hearing aid including a signal converter, an amplifier, a digital signal processor, a memory, and acoustoelectrical input and output transducers. The programmable digital hearing aid is operable in a mode for tinnitus therapy using a tinnitus masking method. U.S. Pat. No. 6,610,019 entitled 'Method and device for treatment of monofrequency tinnitus utilizing sound wave cancellation techniques' discloses a method and device for treating monofrequency tinnitus patients utilizing wave cancellation techniques, which includes a sound generator, a pair of headphones, and a phase shift network. Also, the patent discloses another device including a means for selectively coupling a phase shifted output wave to remove a tinnitus tone transmitted to a patient. U.S. Pat. No. 6,682,472 entitled 'Tinnitus rehabilitation device and method' discloses a device and method which provide an audio signal spectrally modified in accordance with a predetermined masking algorithm designed to modify the intensity of the audio signal at a selected frequency, and this tinnitus rehabilitation device may be employed in conjunction with a personal music player.

However, since the related art does not consider the hearing characteristics of individuals, and attempts to uniformly treat tinnitus patients having different symptoms, a therapy suitable for each patient cannot be provided.

SUMMARY OF THE INVENTION

The present invention provides a method and device for treating tinnitus, which interprets the hearing characteristics of a user, selects either a tinnitus masking method or a tinnitus retraining therapy according to the frequency range in which the tinnitus occurs, and outputs an audio signal of which the frequency characteristics are adjusted in accordance with the selected tinnitus therapy.

According to an aspect of the present invention, there is provided a method for treating tinnitus, comprising: a) generating pure sounds, each having a predetermined frequency, within an audible range, and waiting for a user to press an input button when the user hears the pure sound; b) interpreting hearing characteristics of the user by comparing the result of pressing the input buttons with equal loudness contours; c) selecting either a tinnitus masking method or a tinnitus retraining therapy according to the hearing characteristics of the user; and d) adjusting and outputting the frequency characteristics of a white noise stored in a memory to correspond to the hearing characteristics of the user according to the selected tinnitus therapy.

The operation a) may include: a1) generating a pure sound of a predetermined frequency within an audible range; a2) outputting the pure sound to be increasingly louder and detecting the volume of the pure sound heard by the user from the pressing result of the input buttons when the user hears the pure sound or perceives the pure sound that the user is hearing as being suddenly louder; a3) storing the frequency and volume of the pure sound at the time when the user presses the input button; and a4) repeating the operations a1) through a3) while increasing the frequency within the audible range. In the operation a2), the user may press different input buttons whether the user hears the pure sound or the user perceives the pure sound as being suddenly louder. The method may further comprise: displaying the hearing characteristics of the user together with the equal loudness contours on a graph. In the operation c), the user may select either the tinnitus masking method or the tinnitus retraining method. In the operation c), the tinnitus masking method may be selected when the frequency range where the tinnitus occurs is smaller than a threshold, and the tinnitus retraining method is selected when the frequency range is larger than the threshold.

According to another aspect of the present invention, there is provided a device for treating tinnitus, comprising: a pure sound generating unit which generates pure sounds, each having a predetermined frequency within an audible range; a key input unit for receiving a user's input when the user hears the pure sound; a control unit which interprets the hearing characteristics of the user by comparing the input of the user with equal loudness contours; and an equalizer which adjusts and outputs the frequency characteristics of a white noise stored in a memory according to the interpreted hearing characteristics of the user.

The pure sound generating unit may include: a frequency modulating unit which modulates the frequency of the pure sound; and a volume control unit which controls volume of the pure sound. The key input unit may include: a first input button which receives the input of the user when the user hears the pure sound for the first time; and a second input button which receives the input of the user when the user perceives the pure sound as being suddenly louder. The control unit may select either the tinnitus masking method or the tinnitus retraining method based on the frequency range where the tinnitus occurs based on the interpreted hearing characteristics of the user. The device may further comprise: a timer for performing tinnitus therapy operation for a predetermined period of time. The device may further comprise: a display unit which displays the hearing characteristics of the user together with equal loudness contours on a graph. The device may be mounted in a portable audio player.

BRIEF DESCRIPTION OF THE DRAWINGS

The above and other aspects of the present invention will become more apparent by describing in detail exemplary embodiments thereof with reference to the attached drawings in which.

DETAILED DESCRIPTION OF EXEMPLARY EMBODIMENTS OF THE INVENTION

Figure 1:
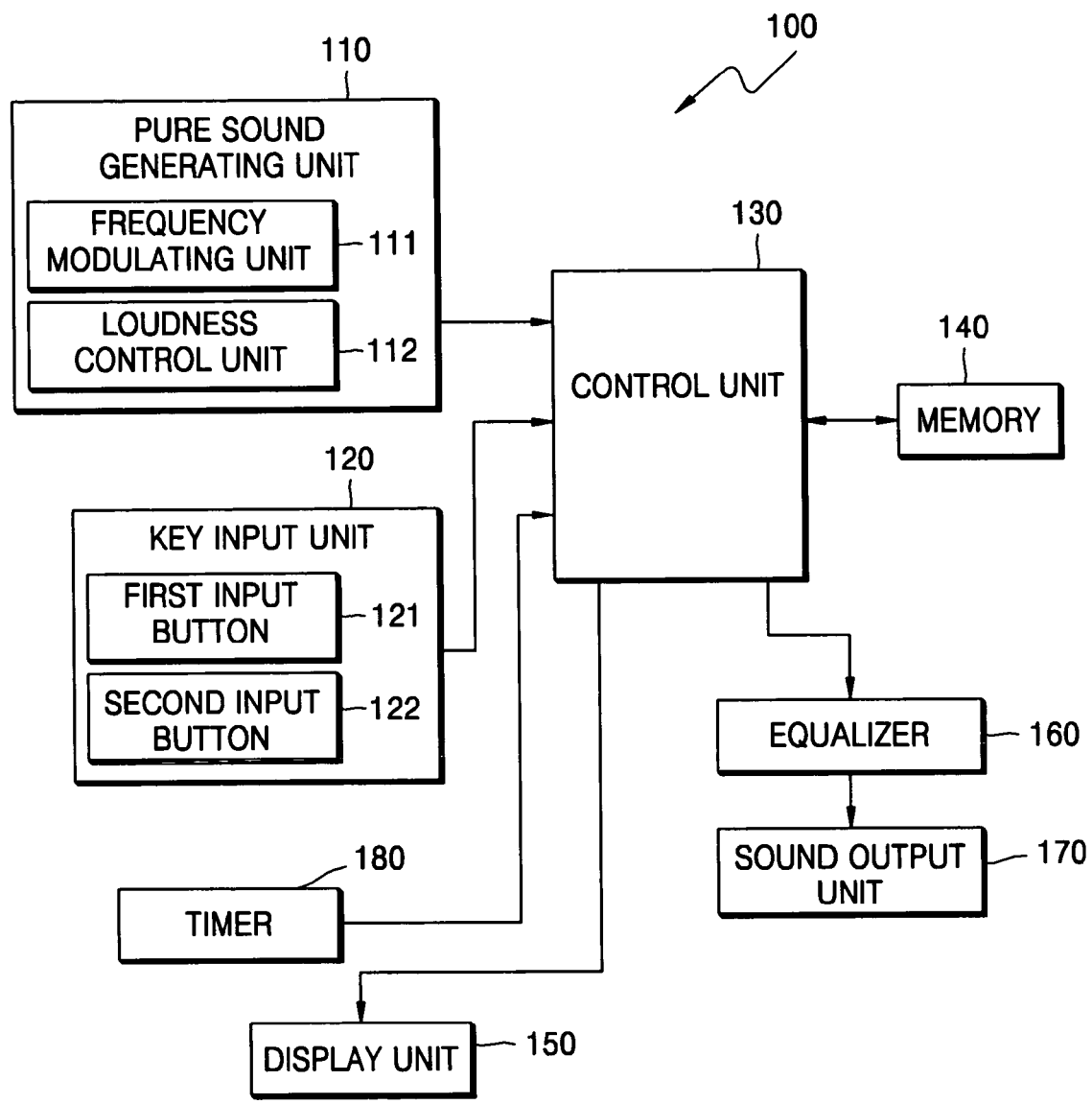
FIG. 1 is a block diagram of a device for treating tinnitus according to an exemplary embodiment of the present invention.

FIG. 1 is a block diagram of a tinnitus treatment device 100 according to an exemplary embodiment of the present invention. Referring to FIG. 1, the tinnitus treatment device 100 includes a pure sound generating unit 110, a key input unit 120, a control unit 130, a memory 140, a display unit 150, an equalizer 150, and an sound output unit 170.

The tinnitus treatment device 100, for example, may be mounted in a portable digital audio player such as a mobile communication terminal (e.g. a mobile phone, a personal digital assistant (PDA)), an MPEG audio layer-3 (MP3) player, or a compact disk (CD) player.

The pure sound generating unit 110 generates pure sounds of a certain frequency. The pure sound, which is composed of frequency components that are not present in the natural world, is generally a sine wave. The pure sound generating unit 110 includes a frequency modulating unit 111 and a volume control unit 112. The frequency modulating unit 111 modulates the frequency within the audible frequency range of 20-20,000 Hz. The volume control unit 112 increases the volume of sound until an input is received from a user through the key input unit 120.

The key input unit 120 is used when the user turns the tinnitus treatment device 100 on and off, and also when the user selects either a tinnitus masking method or a tinnitus retraining therapy. Further, the key input unit 120 includes a first input button 121 and a second input button 122. When the user hears a pure sound generated by the pure sound generating unit 110 through the sound output unit 170, the user presses the first input button 121 when the user hears a sound that has not been perceived before and presses the second input button 122 when a sound that the user is hearing is perceived as being louder. If the tinnitus treatment device 100 is installed in a mobile communication terminal, then when a call is received, the tinnitus treatment operation can be stopped by pressing a call button installed in the key input unit 120.

The control unit 130 compares the frequency and volume signal of the pure sound from the pure sound generating unit 110 with equal loudness contours to interpret the hearing characteristics of the user, when the first input button 121 and the second input button 122 are pressed.

Even if the physical loudness levels of sounds are equal, a sensitivity of human hearing is different depending on frequency. The equal loudness contours are obtained from experiments to find out such human hearing characteristics.

Further, the control unit 130 calculates a frequency range in which tinnitus occurs. According to the frequency range of the tinnitus, the method for tinnitus therapy may be selected. When the frequency range of the tinnitus is relatively small, a tinnitus masking method is used, and when the frequency range of the tinnitus is relatively wide, a tinnitus retraining method is used. A standard of selecting is obtained experimentally, and, for example, the method for tinnitus therapy may be selected based on whether the frequency range of the tinnitus is over or below 500 Hz.

When the tinnitus masking method is selected, the control unit 130 determines a frequency range to be wider than the frequency range in which tinnitus occurs, and the volume of a sound to be louder than the tinnitus sound.

The memory 140 stores a white noise, which is used for a method for tinnitus therapy, as a sound source.

The display unit 150 displays a graph showing the user's hearing characteristics, compared with the equal loudness contours, under the control of the control unit 130.

The equalizer 160, which controls the frequency characteristics of an audio signal, controls an audio signal of a frequency range wider than the frequency range in which the tinnitus occurs to be louder than the tinnitus sound, when the tinnitus masking method is selected, and controls an audio signal such that the user can perceive the audio signal to be same as the tinnitus sound in the entire frequency range when the tinnitus retraining therapy is selected. For the tinnitus masking method, only the frequency range determined in the control unit 130 is increased. Although not illustrated in FIG. 1, a filter and an amplifier may perform this procedure.

The sound output unit 170 converts the audio signal controlled by the equalizer 160 into an analog signal that the user can hear, and outputs the analog signal.

The timer 180 allows the tinnitus treatment device 100 to be operated for a set time.

Figure 2:
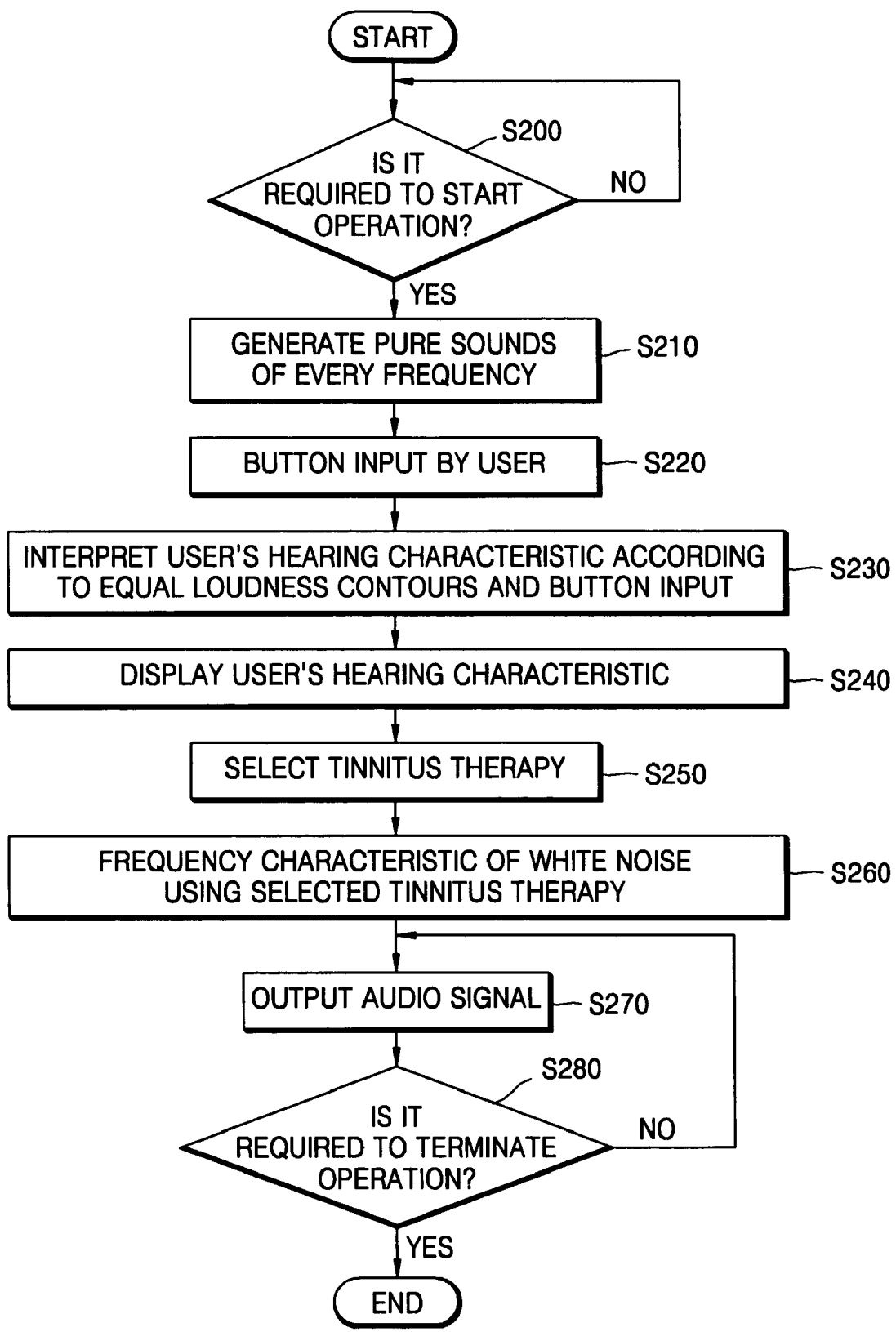
FIG. 2 is a flowchart illustrating a method of treating tinnitus according to an exemplary embodiment of the present invention.

FIG. 2 is a flowchart illustrating a method of treating tinnitus according to an exemplary embodiment of the present invention, which will be described in conjunction with the elements of FIG. 1.

Referring to FIG. 2, in operation S200, it is determined whether the tinnitus treatment device 100 is requested to start operating. The operation is started in response to an operation start command received through the key input unit 120 from a user. Further, although not illustrated, the treatment operation can be stopped according to a stop command through the key input unit 120, at any time during the operation of the tinnitus treatment device 100.

In operation S210, a pure sound is generated for each frequency within the audible range, and in operation S220, a user presses a button of the key input unit 120 when they can hear the pure sound. Operations S210 and S220 are described in detail with reference to FIG. 3.

Figure 3:
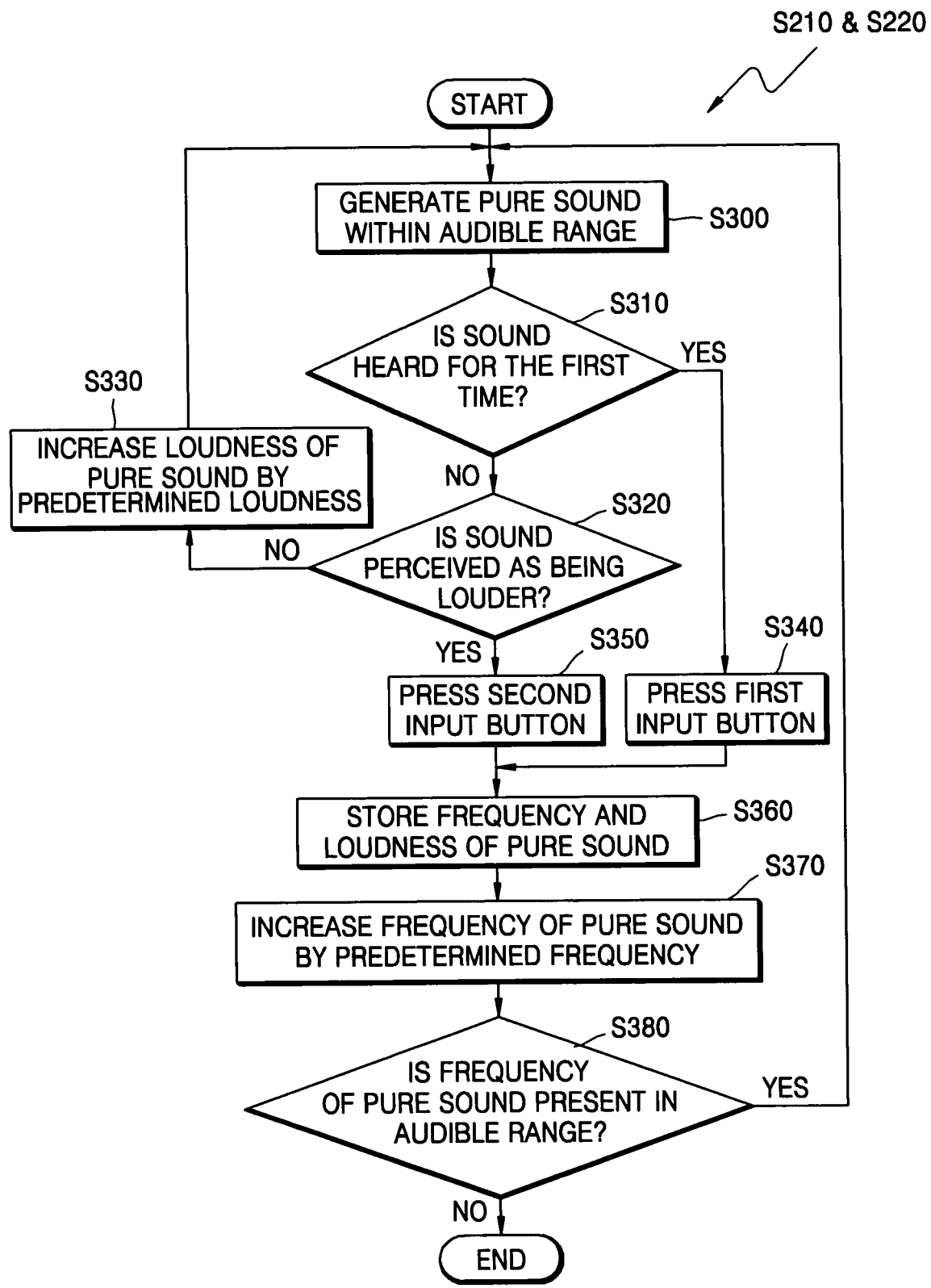
FIG. 3 is a flowchart illustrating in detail operations S220 and S210 of FIG. 2.

FIG. 3 is a flowchart illustrating in detail the operations S210 and S220.

Referring to FIG. 3, in operation S300, a pure sound in the audible range is generated. In operation S330, the loudness of the pure sound is increased by a predetermined loudness and the pure sound is continuously produced unless the user hears a sound that he/she has not perceived before in operation S310 and the sound that the user is hearing is perceived as being louder in operation S320. When hearing the sound the user has not heard before, the user presses the first button in operation S340. When the user perceives the sound he/she is hearing as being louder, the user presses the second input button in operation S350. When the first or second input button is pressed, in operation S360, the frequency and volume of the pure sound that was generated when the button was pressed are stored. In operation S370, the frequency of the pure sound is increased by a predetermined frequency. In operation S380, when the frequency of the pure sound is present within the audible range, the procedure proceeds to operation S300 to generate a pure sound of the increased frequency.

Figure 4A:
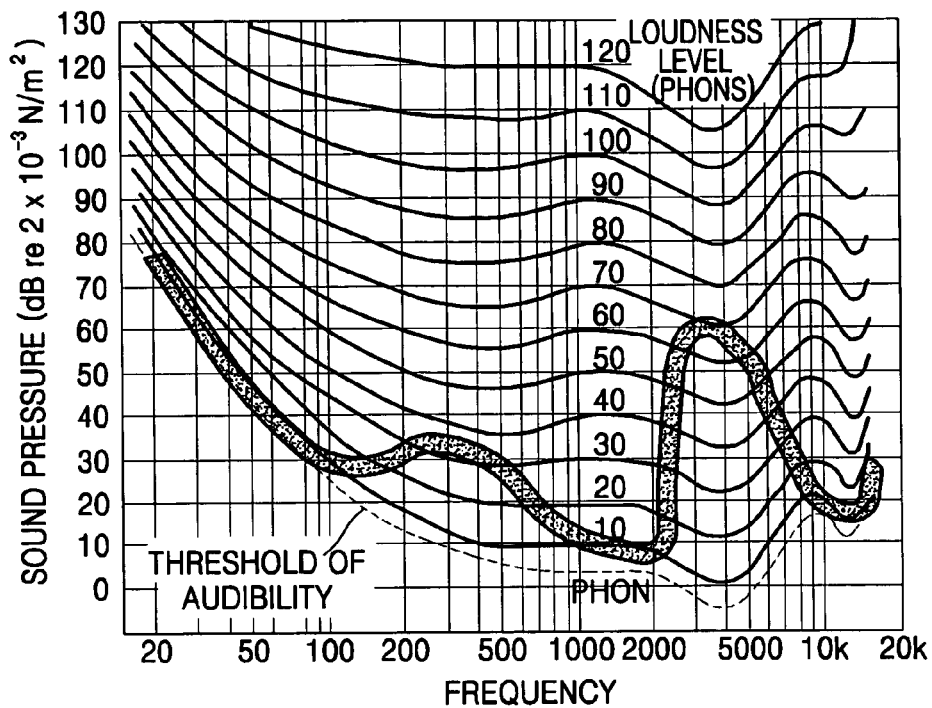
FIGS. 4A-4D are graphs showing experimental results of the method of treating tinnitus according to an exemplary embodiment of the present invention.
Figure 4B:
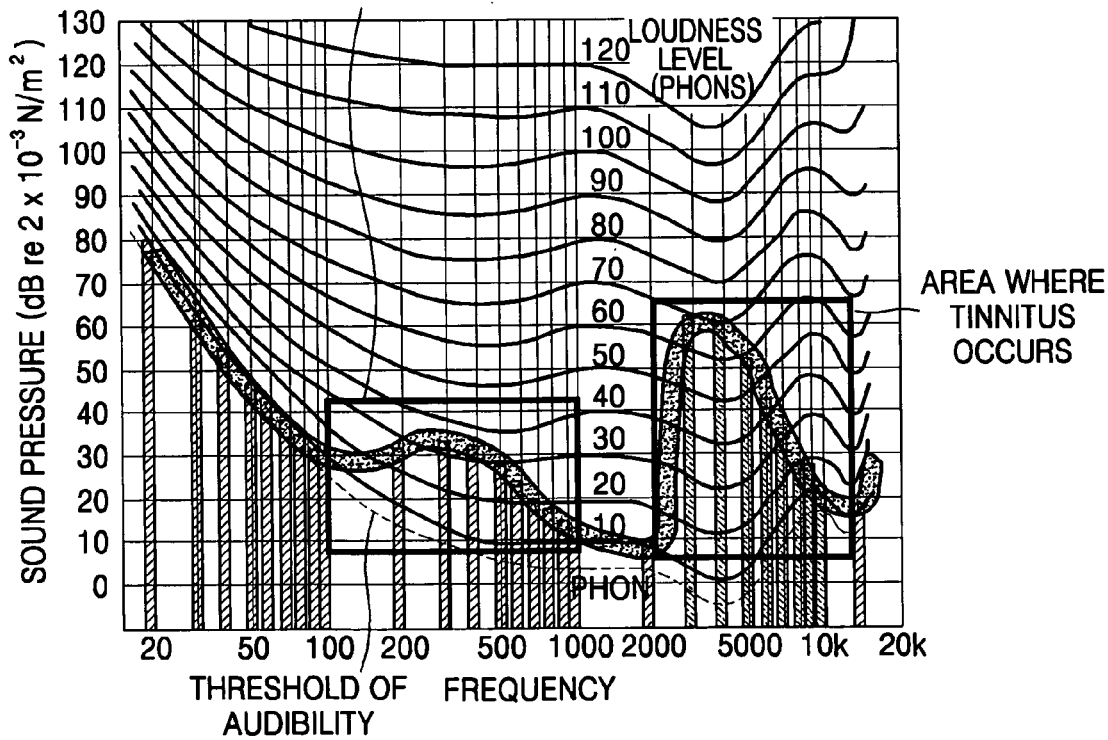

Returning to FIG. 2, in operation S230, the hearing characteristics of the user are interpreted by comparing the frequency and volume of the pure sound that is stored in the memory 140 through the button input from the user with the equal loudness contours. FIG. 4A is a graph showing the hearing characteristics of a user with equal loudness contours. FIG. 4B is a graph showing the result of interpreting the hearing characteristics of the user shown in FIG. 4A. Different shading denotes cases where the first input button is pressed and the second input button is pressed. The area where there is a difference between the hearing characteristics and the equal loudness contour when the first button is pressed is interpreted as an area where the impairment of hearing is present, and the area where there is a difference between the hearing characteristics and the equal loudness contour when the second input button is pressed is interpreted as an area where tinnitus is present.

In operation S240, the hearing characteristics of the user are displayed together with the equal loudness contours. In operation S250, the method for tinnitus therapy is selected. The user can select the tinnitus masking method or the tinnitus retraining therapy after viewing his/her hearing characteristics. Alternatively, the control unit 130 can automatically select the method for tinnitus therapy according to the hearing characteristics of the user.

Figure 4C:
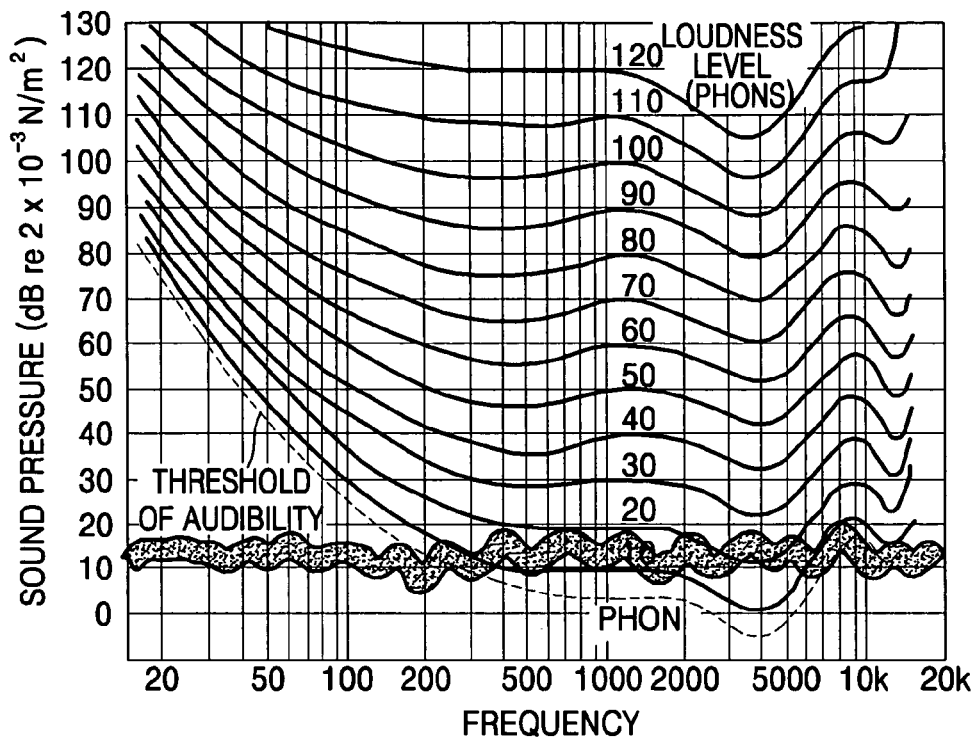
Figure 4D:
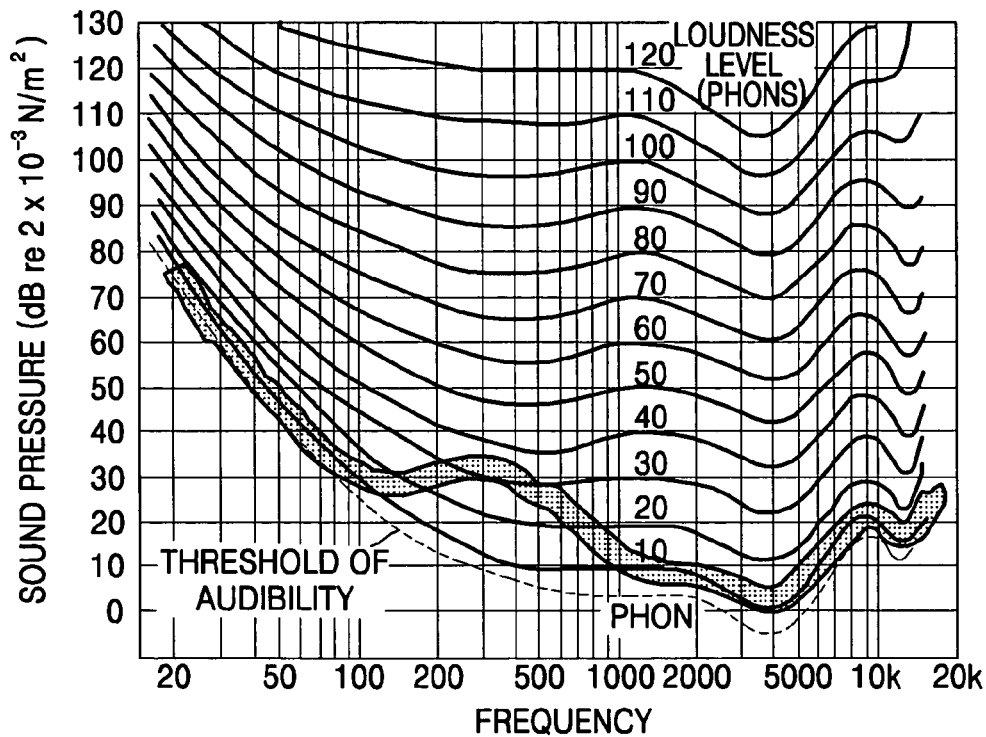

In operation S260, the frequency characteristics of the white noise stored in the memory 140 are adjusted according to the selected method for tinnitus therapy. For the tinnitus masking method, a signal of a frequency range wider than the frequency range where the tinnitus is present is generated louder than the tinnitus sound, and the frequency range and volume of the signal are experimentally determined. After only a frequency range to mask the tinnitus is filtered by a band pass filter, the volume is properly amplified. For the tinnitus retraining therapy, the frequency characteristics are adjusted such that the user can perceive sounds in the entire frequency range as being the same, and then the sound is output. Unlike the tinnitus masking method, a signal in the frequency range where the tinnitus is present is removed through a band rejection filter, and then the volume is properly amplified. FIG. 4C shows a white noise stored in the memory, and FIG. 4D is the result of adjusting the frequency characteristics to correspond to the user's hearing characteristic.

In operation S270, a sound signal of which the frequency characteristics have been adjusted is output. In operation S280, the tinnitus therapy operation is terminated according to the user's operation end command. Further, even if there is no operation end command of the user, when the operation time set by the timer 180 is reached, the tinnitus therapy operation is terminated.

According to the present invention, the hearing characteristics of a user are interpreted, and either a tinnitus masking method or a tinnitus retraining therapy is selected according to the frequency range where the tinnitus occurs. Then, a sound signal is adjusted using the selected tinnitus therapy and output, to efficiently treat the tinnitus.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method for treating tinnitus, comprising:
 a) generating pure sounds and waiting for a user to press an input button when the user hears the pure sound;
 b) interpreting hearing characteristics of the user by comparing the result of pressing the input buttons device with equal loudness contours;
 c) selecting either a tinnitus masking method or a tinnitus retraining therapy according to the hearing characteristics of the user; and
 d) adjusting and outputting frequency characteristics of a white noise stored in a memory to correspond to the hearing characteristics of the user according to the selected tinnitus therapy,
 wherein the operation a) includes:
 a1) generating a pure sound of a predetermined frequency within an audible range;
 a2) outputting the pure sound to be increasingly louder and detecting the volume of the pure sound heard by the user from the pressing result of the input buttons when the user hears the pure sound or perceives the pure sound that the user is hearing as being suddenly louder;
 a3) storing the frequency and volume of the pure sound at the time when the user presses the input button; and
 a4) repeating the operations a1) through a3) while increasing the frequency within the audible range,
 wherein in the operation a2), the user presses different input buttons whether the user hears the pure sound or the user perceives the pure sound as being suddenly louder,
 wherein in operation c), the tinnitus masking method is selected when a frequency range where the tinnitus occurs is narrower than a threshold, and the tinnitus retraining method is selected when the frequency range is wider than the threshold.

2. The method of claim 1, further comprising:
 displaying the hearing characteristics of the user together with the equal loudness contours on a graph.

3. The method of claim 1, wherein the pure sounds each have a predetermined frequency within an audible range.

4. A device for treating tinnitus, comprising:
 a pure sound generating unit which generates pure sounds;
 an input unit for receiving a user's input when the user hears the pure sound;
 a control unit which interprets the hearing characteristics of the user by comparing the input of the user with equal loudness contours; and
 an equalizer which adjusts and outputs the frequency characteristics of a white noise stored in a memory according to the interpreted hearing characteristics of the user,
 wherein the control unit selects either a tinnitus masking method or a tinnitus retraining method based on a frequency range where the tinnitus occurs based on the interpreted hearing characteristics of the user, wherein the pure sound generating unit includes:

a frequency modulating unit which modulates the frequency of the pure sound; and a volume control unit which controls volume of the pure sound, wherein the input unit includes:

a first input button which receives the input of the user when the user hears the pure sound for the first time; and a second input button which receives the input of the user when the user perceives the pure sound as being suddenly louder.

5. The device of claim 4, further comprising:

a timer for performing tinnitus therapy operation for a predetermined period of time.

6. The device of claim 4, further comprising:

a display unit which displays the hearing characteristics of the user together with equal loudness contours on a graph.

7. The device of claim 4, mounted in a portable audio player.

8. The device of claim 4, wherein the pure sounds each have a predetermined frequency within an audible range.

* * * * *